(12) United States Patent
Baker et al.

(10) Patent No.: US 6,569,429 B1
(45) Date of Patent: May 27, 2003

(54) HUMAN DNASE II

(75) Inventors: Kevin P. Baker, San Mateo, CA (US); Will F. Baron, Brisbane, CA (US)

(73) Assignee: Genentech, Inc., South San Francisco, CA (US)

( * ) Notice: Subject to any disclaimer, the term of this patent is extended or adjusted under 35 U.S.C. 154(b) by 0 days.

(21) Appl. No.: 09/861,034

(22) Filed: May 18, 2001

Related U.S. Application Data

(62) Division of application No. 08/639,294, filed on Apr. 25, 1996, now Pat. No. 6,265,195.

(51) Int. Cl.[7] ............... A61K 38/46; C12N 9/16; C12N 9/22; C12N 1/20; C07H 21/04
(52) U.S. Cl. ............ 424/94.6; 435/196; 435/199; 435/252.3; 435/320.1; 536/23.2
(58) Field of Search ................... 435/196, 199, 435/252.3, 320.1; 536/23.2; 424/94.6

(56) References Cited

PUBLICATIONS

Harosh et al., "Mechanism of action of deoxyribonuclease II from human lymphoblasts" *European Journal of Biochemistry* 202:479–484 (1991).

Murai et al., "Purification and Properties of Deoxyribonuclease II from Human Urine" *J. Biochem.* 87:1097–1103 (1980).

Sambrook et al. *Molecular Cloning: A Laboratory Manual*, Cold Spring Harbor Lab Press pps. 11.3–11.19 (1989).

*Primary Examiner*—Tekchand Saidha
(74) *Attorney, Agent, or Firm*—David W Evans

(57) ABSTRACT

This invention relates to a novel human deoxyribonuclease, referred to as human DNase II. The invention provides nucleic acid sequences encoding human DNase II, thereby enabling the production of human DNase II by recombinant DNA methods in quantities sufficient for clinical use. The invention also relates to pharmaceutical compositions and diagnostic and therapeutic uses of human DNase II.

4 Claims, 2 Drawing Sheets

```
  1 GAATTCGGGCCAGTCCTGGCCTCTGATG TAA CCCAGCGCCCCGCAGTCCCGACACAGATT

61 CCTGGATCTCAGCCCCATAGCAGCTATGATCCCGCTGCTGCTGGCAGCGCTGCTGTGCGT
-16                              M  I  P  L  L  L  A  A  L  L  C  V

121 CCCCGCCGGGGCCCTGACCTGCTACGGGGACTCCGGGCAGCCTGTAGACTGGTTCGTGGT
 -4  P  A  G  A  L  T  C  Y  G  D  S  G  Q  P  V  D  W  F  V  V
                   ▲        *

181 CTACAAGCTGCCAGCTCTTAGAGGGTCCGGGGAGGCGGCGCAGAGAGGGCTGCAGTACAA
 17  Y  K  L  P  A  L  R  G  S  G  E  A  A  Q  R  G  L  Q  Y  K

241 GTATCTGGACGAGAGCTCCGGAGGCTGGCGGGACGGCAGGGCACTCATCAACAGCCCGGA
 37  Y  L  D  E  S  S  G  G  W  R  D  G  R  A  L  I  N  S  P  E

301 GGGGGCCGTGGGCCGAAGCCTGCAGCCGCTGTACCGGAGCAACACCAGCCAGCTCGCCTT
 57  G  A  V  G  R  S  L  Q  P  L  Y  R  S  N  T  S  Q  L  A  F

361 CCTGCTCTACAATGACCAACCGCCTCAACCCAGCAAGGCTCAGGACTCTTCCATGCGTGG
 77  L  L  Y  N  D  Q  P  P  Q  P  S  K  A  Q  D  S  S  M  R  G

421 GCACACGAAGGGTGTCCTGCTCCTTGACCACGATGGGGGCTTCTGGCTGGTCCACAGTGT
 97  H  T  K  G  V  L  L  L  D  H  D  G  G  F  W  L  V  H  S  V

481 ACCTAACTTCCCTCCACCGGCCTCCTCTGCTGCATACAGCTGGCCTCATAGCGCCTGTAC
117  P  N  F  P  P  P  A  S  S  A  A  Y  S  W  P  H  S  A  C  T
                                                              *

541 CTACGGGCAGACCCTGCTCTGTGTGTCTTTTCCCTTCGCTCAGTTCTCGAAGATGGGCAA
137  Y  G  Q  T  L  L  C  V  S  F  P  F  A  Q  F  S  K  M  G  K
                   *

601 GCAGCTGACCTACACCTACCCCTGGGTCTATAACTACCAGCTGGAAGGGATCTTTGCCCA
157  Q  L  T  Y  T  Y  P  W  V  Y  N  Y  Q  L  E  G  I  F  A  Q

661 GGAATTCCCCGACTTGGAGAATGTGGTCAAGGGCCACCACGTTAGCCAAGAACCCTGGAA
177  E  F  P  D  L  E  N  V  V  K  G  H  H  V  S  Q  E  P  W  N

721 CAGCAGCATCACACTCACATCCCAGGCCGGGGCTGTTTTCCAGAGCTTTGCCAAGTTCAG
197  S  S  I  T  L  T  S  Q  A  G  A  V  F  Q  S  F  A  K  F  S

781 CAAATTTGGAGATGACCTGTACTCCGGCTGGTTGGCAGCAGCCCTTGGTACCAACCTGCA
217  K  F  G  D  D  L  Y  S  G  W  L  A  A  A  L  G  T  N  L  Q

841 GGTCCAGTTCTGGCACAAAACTGTAGGCATCCTGCCCTCTAACTGCTCGGATATCTGGCA
237  V  Q  F  W  H  K  T  V  G  I  L  P  S  N  C  S  D  I  W  Q
                                                       *

901 GGTTCTGAATGTGAACCAGATAGCTTTCCCTGGACCAGCCGGCCCAAGCTTCAACAGCAC
257  V  L  N  V  N  Q  I  A  F  P  G  P  A  G  P  S  F  N  S  T
```

FIG._1A

```
961  AGAGGACCACTCCAAATGGTGCGTGTCCCCAAAAGGGCCCTGGACCTGCGTGGGTGACAT
277   E   D   H   S   K   W   C   V   S   P   K   G   P   W   T   C   V   G   D   M
                              *                                           *

1021 GAATCGGAACCAGGGAGAGGAGCAACGGGGTGGGGGCACACTGTGTGCCCAGCTGCCAGC
297   N   R   N   Q   G   E   E   Q   R   G   G   G   T   L   C   A   Q   L   P   A
                                                          *

1081 CCTCTGGAAAGCCTTCCAGCCGCTGGTGAAGAACTACCAGCCCTGTAATGGCATGGCCAG
317   L   W   K   A   F   Q   P   L   V   K   N   Y   Q   P   C   N   G   M   A   R
                                                          *

1141 GAAGCCCAGCAGAGCTTATAAGATCTAACCCTTATGGCCAGGTGCAGTGGCTCACGTATG
337   K   P   S   R   A   Y   K   I

1201 TAATCCCAGCACTTTGGGAAGCCAAGGAGGGAGGATCACTTGAACTCAGGAATTCGAGAC

1261 CAGCCTGGGCTACATAGTGAGACCACATCTCTACTAGAACTTAAAAAAAGTTAGCCAGGC

1321 ACGGTGATAAATGCCTGTAGTCCCAGCCACTGAAGCCAGAGGATCGATTGAACCAGGGAG

1381 ATCATGGTCACAGTGAACTATGATTACGCCAACCTGGGTCACATAGCAAGACTCTGTTTC

1441 AAAAAAAAGGGGGGCGGGGGACGGGTGGGTGCAGTGGCTCACATCTGTAACCCCAGCA

1501 CTTTGGGAGGCTGAGATGGGCAGATCACTTGAGGTCAGGAGTTCGAGACCAGCCTGGCCA

1561 ACATGGTGAAACCCC
```

FIG._1B

HUMAN DNASE II

This is a divisional Ser. No. 08/639,294 filed on Apr. 25, 1996, now U.S. Pat. No. 6,265,195, which application is incorporated herein by reference and to which application priority is claimed under 35 USC §120.

FIELD OF THE INVENTION

The present invention relates to newly identified human deoxyribonuclease (DNase) protein, nucleic acid encoding such protein, the use of such protein and nucleic acid, as well as the production of such protein and nucleic acid, for example, by recombinant DNA methods.

BACKGROUND OF THE INVENTION

Deoxyribonuclease (DNase) is a phosphodiesterase capable of hydrolyzing polydeoxyribonucleic acid, and is known to occur in several molecular forms. Based on their biochemical properties and enzymatic activities, DNase proteins have been classified as two types, DNase I and DNase II. DNase I proteins have a pH optimum near neutrality, an obligatory requirement for divalent cations, and produce 5'-phosphate nucleotides on hydrolysis of DNA. DNase II proteins exhibit an acid pH optimum, do not require divalent cations for activity, and produce 3'-phosphate nucleotides on hydrolysis of DNA.

DNase from various species have been purified to a varying degree. For example, various forms of bovine DNase I have been purified and completely sequenced (Liao, et al., J. Biol. Chem. 248:1489–1495 (1973); Oefner, et al., J. Mol. Biol. 192:605–632 (1986); Lahm, et al., J. Mol. Biol. 221:645–667 (1991)), and DNA encoding bovine DNase I has been cloned and expressed (Worrall, et al., J. Biol. Chem 265:21889–21895 (1990)). Porcine and orcine DNase I proteins also have been purified and completely sequenced (Paudel, et al., J. Biol. Chem. 261:16006–16011 (1986); Paudel, et al., J. Biol. Chem. 261:16012–16017 (1986)).

DNA encoding a human DNase I has been isolated and sequenced and the DNA has been expressed in recombinant host cells, thereby enabling the production of human DNase I in commercially useful quantities. Shak, et al., Proc. Natl. Acad. Sci. 87:9188–9192 (1990). The term "human DNase I" will be used hereafter to refer to the mature polypeptide disclosed in Shak, et al.

DNA encoding other polypeptides having homology to human DNase I also have been identified. Rosen, et al., PCT Patent Publication No. WO 95/30428, published Nov. 16, 1995; Parrish, et al., Hum. Mol. Genet. 4:1557–1564 (1995); Baker, et. al., U.S. patent application Ser. No. 08/597,078 (filed Feb. 5, 1996).

DNase I has a number of known utilities and has been used for therapeutic purposes. Its principal therapeutic use has been to reduce the viscoelasticity of pulmonary secretions (including mucus) in such diseases as pneumonia and cystic fibrosis (CF), thereby aiding in the clearing of respiratory airways. See e.g., Lourenco, et al., Arch. Intern. Med. 142:2299–2308 (1982); Shak, et al., Proc. Natl. Acad. Sci. 87:9188–9192 (1990); Hubbard, et al., New Engl. J. Med. 326:812–815 (1992); Fuchs, et al., New Engl. J. Med. 331:637–642 (1994); Bryson, et al., Drugs 48:894–906 (1994). Mucus also contributes to the morbidity of chronic bronchitis, asthmatic bronchitis, bronchiectasis, emphysema, acute and chronic sinusitis, and even the common cold. DNase I is effective in reducing the viscoelasticity of pulmonary secretions by hydrolyzing, or degrading, high-molecular-weight DNA that is present in such secretions. Shak, et al., Proc. Natl. Acad. Sci. 87:9188–9192 (1990); Aitken, et al., J. Am. Med. Assoc. 267:1947–1951 (1992).

Various forms of DNase II also have reportedly been purified, including bovine DNase II (Lesca, J. Biol. Chem. 251:116–123 (1976)), human DNase II (Yamanaku, et al., J. Biol. Chem. 249:3884–3889 (1974); Murai, et al., J. Biochem. 87:1097–1103 (1980); Harosh, et al., Eur. J. Biochem. 202:479–484 (1991); Yasuda, et al., Biochem. Biophys. Acta 1119:185–193 (1992)), porcine DNase II (Bernardi, et al., Biochemistry 4:1725–1729 (1965); Liao, et al., J. Biol. Chem. 260:10708–10713 (1990)), and rat DNase II (Dulaney, et al., J. Biol. Chem. 247:1424–1432 (1972)). The physical properties of the human DNase II proteins described in these reports vary considerably (e.g., reported molecular weights range from 32,000 to 45,000 Daltons), which leads to uncertainty whether there is one or multiple naturally occurring forms of the human protein.

Recent interest in human DNase II has arisen because of its possible role in the programmed cell death process of apoptosis (Barry, et al., Arch. Biochem. Biophys. 300:440–450 (1993); Barry, et al., Cancer Res. 53:2349–2357 (1993)). One of the events that is characteristic of that process is the degradation of nuclear DNA into nucleosomal fragments. The ability to prevent or inhibit the expression of human DNase II or its enzymatic activity within human cells may be important in preventing or limiting such intracellular destruction of DNA, and thus may be an effective means of interrupting the process of apoptosis. In other instances, it may be useful to increase the expression of human DNase II within a certain population of cells within a human patient, such as cancer cells, in order to induce apoptosis of those cells.

SUMMARY OF THE INVENTION

The present invention provides human DNase II protein, as well as analogs and variants thereof, that have DNA-hydrolytic activity. As is characteristic of DNase II proteins in general, the human DNase II of the present invention exhibits an acid pH optimum, and does not require divalent cation for activity.

The invention also provides nucleic acids encoding human DNase II, recombinant vectors comprising such nucleic acids, recombinant host cells transformed with those nucleic acids or vectors, and processes for producing human DNase II by means of recombinant DNA technology. The invention includes the use of such nucleic acids and vectors for in vivo or ex vivo gene therapy.

The invention also provides complementary nucleic acids, including so-called anti-sense oligonucleotides, that are capable of binding to and preventing the expression of nucleic acid within a cell that encodes human DNase II.

The invention also provides pharmaceutical compositions comprising human DNase II, optionally together with a pharmaceutically acceptable excipient, as well as substantially purified antibodies that are capable of binding to human DNase II.

The invention also provides methods for reducing the viscoelasticity or viscous consistency of DNA-containing material in a patient, comprising administering a therapeutically effective dose of human DNase II to the patient. The invention is particularly directed to a method of treating a patient having a disease such as cystic fibrosis, chronic bronchitis, pneumonia, bronchiectasis, emphysema, asthma, or systemic lupus erythematosus, that comprises administering a therapeutically effective amount of human DNase II to the patient. The invention also is directed to the use of human DNase II in vitro, such as for degrading DNA that is present in a biological specimen or other material, and in diagnostic and other assays.

These and other aspects of the invention will be apparent to the ordinary skilled artisan upon consideration of the following detailed description.

BRIEF DESCRIPTION OF THE FIGURES

FIGS. 1A–1B show the nucleotide sequence (SEQ. ID. NO: 1) and deduced amino acid sequence (SEQ. ID. NO: 2) of human DNase II. The predicted leader (signal amino acid sequence is underlined and the start of the mature protein is indicated by the arrowhead. The eight cysteine residues are indicated by asterisks and potential N-linked glycosylation sites are boxed.

DETAILED DESCRIPTION

The various aspects of the present invention are accomplished by first providing isolated DNA comprising the nucleotide coding sequence for human DNase II. By providing the full nucleotide coding sequence for human DNase II, the invention enables the production of human DNase II by means of recombinant DNA technology, thereby making available for the first time sufficient quantities of substantially pure human DNase II protein for diagnostic and therapeutic uses.

As used herein, the term "human DNase II" refers to the polypeptide having the amino acid sequence of the mature protein set forth in FIG. 1 as well as modified and variant forms thereof as described herein. Modified and variant forms of human DNase II are produced in vitro by means of chemical or enzymatic treatment or in vivo by means of recombinant DNA technology. Such polypeptides differ from human DNase II, for example, by virtue of one or more amino acid substitutions, insertions, and/or deletions, or in the extent or pattern of glycosylation, but in all cases will possess DNA-hydrolytic activity. A "variant" or "amino acid sequence variant" of human DNase II is a polypeptide that comprises an amino acid sequence different from that of human DNase II. Generally, a variant will have at least 80% sequence identity, preferably at least 90% sequence identity, more preferably at least 95% sequence identity, and most preferably at least 98% sequence identity with human DNase II. Percentage sequence identity is determined, for example, by the Fitch, et al., Proc. Natl. Acad. Sci. USA 80:1382–1386 (1983), version of the algorithm described by Needleman, et al., J. Mol. Biol. 48:443–453 (1970), after aligning the sequences to provide for maximum homology. Such variants include naturally occurring allelic forms of human DNase II that are of human origin as well as naturally occurring homologs of human DNase II that are found in other animal species.

"DNA-hydrolytic activity" refers to the enzymatic activity of human DNase II in hydrolyzing (cleaving) substrate DNA to yield 3'-phosphorylated oligonucleotide end products. DNA-hydrolytic activity is readily determined by any of several different methods known in the art, including analytical polyacrylamide and agarose gel electrophoresis, hyperchromicity assay (Kunitz, J. Gen. Physiol. 33:349–362 (1950); Kunitz, J. Gen. Physiol. 33:363–377 (1950)), or methyl green assay (Kurnick, Arch. Biochem. 29:41–53 (1950); Sinicropi, et al., Anal. Biochem. 222:351–358 (1994)). As a routine matter, the pH and buffer used in these methods are varied so as to provide the conditions wherein the particular human DNase II will exhibit such activity, if any.

For convenience, substitutions, insertions, and/or deletions in the amino acid sequence of human DNase II are usually made by introducing mutations into the corresponding nucleotide sequence of the DNA encoding human DNase II, for example by site-directed mutagenesis. Expression of the mutated DNA then results in production of the variant human DNase II, having the desired amino acid sequence.

Whereas any technique known in the art can be used to perform site-directed mutagenesis, e.g. as disclosed in Sambrook, et al., *Molecular Cloning: A Laboratory Manual*, Second Edition (Cold Spring Harbor Laboratory Press, New York (1989)), oligonucleotide-directed mutagenesis is the preferred method for preparing the human DNase II variants of this invention. This method, which is well known in the art (Zoller, et al., Meth. Enzymol. 100:4668–500 (1983); Zoller, et al., Meth. Enzymol. 154:329–350 (1987); Carter, Meth. Enzymol. 154:382–403 (1987); Kunkel, et al., Meth. Enzymol. 154:367–382 (1987); Horwitz, et al., Meth. Enzymol. 185:599–611 (1990)), is particularly suitable for making substitution variants, although it may also be used to conveniently prepare deletion and insertion variants, as well as variants having multiple substitution, insertion, and/or deletion mutations.

Briefly, in carrying out site-directed mutagenesis of DNA encoding human DNase II (or a variant thereof), the DNA is altered by first hybridizing an oligonucleotide encoding the desired mutation to a single strand of the DNA. After hybridization, a DNA polymerase is used to synthesize an entire second strand, using the hybridized oligonucleotide as a primer, and using the single strand of the DNA as a template. Thus, the oligonucleotide encoding the desired mutation is incorporated in the resulting double-stranded DNA.

Oligonucleotides may be prepared by any suitable method, such as by purification of a naturally occurring DNA or by in vitro synthesis. For example, oligonucleotides are readily synthesized using various techniques in organic chemistry, such as described by Narang, et al., Meth. Enzymol. 68:90–98 (1979); Brown, et al., Meth. Enzymol. 68:109–151 (1979); Caruthers, et al., Meth. Enzymol. 154:287–313 (1985). The general approach to selecting a suitable oligonucleotide for use in site-directed mutagenesis is well known. Typically, the oligonucleotide will contain 10–25 or more nucleotides, and will include at least 5 nucleotides on either side of the sequence encoding the desired mutation so as to ensure that the oligonucleotide will hybridize preferentially at the desired location to the single-stranded DNA template molecule.

"Polymerase chain reaction," or "PCR," generally refers to a method for amplification of a desired nucleotide sequence in vitro, as described, for example, in U.S. Pat. No. 4,683,195. In general, the PCR method involves repeated cycles of primer extension synthesis, using oligonucleotide primers capable of hybridizing preferentially to a template nucleic acid.

PCR mutagenesis (Higuchi, in *PCR Protocols*, pp.177–183 (Academic Press, 1990); Vallette, et al., Nuc. Acids Res. 17:723–733 (1989)) is also suitable for making the variants of human DNase II. Briefly, when small amounts of template DNA are used as starting material in a PCR, primers that differ slightly in sequence from the corresponding region in the template DNA can be used to generate relatively large quantities of a specific DNA fragment that differs from the template sequence only at the positions where the primers differ from the template. For introduction of a mutation into a plasmid DNA, for example, the sequence of one of the primers includes the desired mutation and is designed to hybridize to one strand of the plasmid DNA at the position of the mutation; the sequence of the other primer must be identical to a nucleotide sequence within the opposite strand of the plasmid DNA, but this sequence can be located anywhere along the plasmid DNA. It is preferred, however, that the sequence of the second primer is located within 200 nucleotides from that of the first, such that in the end the entire amplified region of DNA bounded by the primers can be easily sequenced. PCR amplification using a primer pair like the one just described results in a population of DNA fragments that differ at the position of the mutation specified by the primer, and possibly at other positions, as template copying is somewhat error-prone. Wagner, et al., in PCR Topics, pp.69–71 (Springer-Verlag, 1991).

If the ratio of template to product amplified DNA is extremely low, the majority of product DNA fragments incorporate the desired mutation(s). This product DNA is used to replace the corresponding region in the plasmid that served as PCR template using standard recombinant DNA methods. Mutations at separate positions can be introduced simultaneously by either using a mutant second primer, or performing a second PCR with different mutant primers and ligating the two resulting PCR fragments simultaneously to the plasmid fragment in a three (or more)-part ligation.

Another method for preparing variants, cassette mutagenesis, is based on the technique described by Wells et al., Gene, 34:315–323 (1985). The starting material is the plasmid (or other vector) comprising the DNA sequence to be mutated. The codon(s) in the starting DNA to be mutated are identified. There must be a unique restriction endonuclease site on each side of the identified mutation site(s). If no such restriction sites exist, they may be generated using the above-described oligonucleotide-mediated mutagenesis method to introduce them at appropriate locations in the DNA. The plasmid DNA is cut at these sites to linearize it. A double-stranded oligonucleotide encoding the sequence of the DNA between the restriction sites but containing the desired mutation(s) is synthesized using standard procedures, wherein the two strands of the oligonucleotide are synthesized separately and then hybridized together using standard techniques. This double-stranded oligonucleotide is referred to as the cassette. This cassette is designed to have 5' and 3' ends that are compatible with the ends of the linearized plasmid, such that it can be directly ligated to the plasmid. The resulting plasmid contains the mutated DNA sequence.

The presence of mutation(s) in a DNA is determined by methods well known in the art, including restriction mapping and/or DNA sequencing. A preferred method for DNA sequencing is the dideoxy chain termination method of Sanger, et al., Proc. Natl. Acad. Sci. USA 72:3918–3921 (1979).

DNA encoding human DNase II is inserted into a replicable vector for further cloning or expression. "Vectors" are plasmids and other DNAs that are capable of replicating within a host cell, and as such, are useful for performing two functions in conjunction with compatible host cells (a vector-host system). One function is to facilitate the cloning of nucleic acid that encodes human DNase II, i.e., to produce usable quantities of the nucleic acid. The other function is to direct the expression of human DNase II. One or both of these functions are performed by the vector in the particular host cell used for cloning or expression. The vectors will contain different components depending upon the function they are to perform.

The human DNase II of the present invention may be expressed in the form of a preprotein wherein the DNase II includes a leader or signal sequence, or may be in the form of a mature protein which lacks a leader or signal sequence. The human DNase II also may be in the form of a fusion protein wherein additional amino acid residues are covalently joined to the amino- or carboxy terminus of the preprotein or mature form of the DNase.

To produce human DNase II, an expression vector will comprise DNA encoding human DNase II, as described above, operably linked to a promoter and a ribosome binding site. The human DNase II then is expressed directly in recombinant cell culture, or as a fusion with a heterologous polypeptide, preferably a signal sequence or other polypeptide having a specific cleavage site at the junction between the heterologous polypeptide and the human DNase II amino acid sequence. "Operably linked" refers to the covalent joining of two or more DNA sequences, by means of enzymatic ligation or otherwise, in a configuration relative to one another such that the normal function of the sequences can be performed. For example, DNA for a presequence or secretory leader is operably linked to DNA for a polypeptide if it is expressed as a preprotein that participates in the secretion of the polypeptide; a promoter or enhancer is operably linked to a coding sequence if it affects the transcription of the sequence; or a ribosome binding site is operably linked to a coding sequence if it is positioned so as to facilitate translation. Generally, "operably linked" means that the DNA sequences being linked are contiguous and, in the case of a secretory leader, contiguous and in reading phase. Linking is accomplished by ligation at convenient restriction sites. If such sites do not exist, then synthetic oligonucleotide adaptors or linkers are used, in conjunction with standard recombinant DNA methods.

Prokaryotes (e.g., *E. coli*, strains of Bacillus, Pseudomonas, and other bacteria) are the preferred host cells for the initial cloning steps of this invention. They are particularly useful for rapid production of large amounts of DNA, for production of single-stranded DNA templates used for site-directed mutagenesis, and for DNA sequencing of the variants generated. Prokaryotic host cells also may be used for expression of DNA encoding human DNase II. Polypeptides that are produced in prokaryotic cells typically will be non-glycosylated.

In addition, human DNase II may be expressed in eukaryotic host cells, including eukaryotic microbes (e.g., yeast) or cells derived from an animal or other multicellular organism (e.g., Chinese hamster ovary cells, and other mammalian cells), or in live animals (e.g., cows, goats, sheep). Insect cells and fungii also may be used.

Cloning and expression methodologies are well known in the art. Examples of prokaryotic and eukaryotic host cells, and starting expression vectors, suitable for use in producing human DNase II are, for example, those disclosed in Shak, PCT Patent Publication No. WO 90/07572, published Jul. 12, 1990. To obtain expression of human DNase II, an expression vector of the invention is introduced into host cells by transformation or transfection, and the resulting recombinant host cells are cultured in conventional nutrient media, modified as appropriate for inducing promoters, selecting recombinant cells, or amplifying human DNase II DNA. The culture conditions, such as temperature, pH, and the like, are those previously used with the host cell, and as such will be apparent to the ordinarily skilled artisan.

"Transformation" and "transfection" are used interchangeably to refer to the process of introducing DNA into a cell. Following transformation or transfection, the DNA may integrate into the host cell genome, or may exist as an extrachromosomal element. If prokaryotic cells or cells that contain substantial cell wall constructions are used as hosts, the preferred methods of transfection of the cells with DNA is the calcium treatment method described by Cohen et al., Proc. Natl. Acad. Sci. 69:2110–2114 (1972) or the polyethylene glycol method of Chung et al., Nuc. Acids. Res. 16:3580 (1988). If yeast are used as the host, transfection is generally accomplished using polyethylene glycol, as taught by Hinnen, Proc. Natl. Acad. Sci. U.S.A., 75: 1929–1933 (1978). If mammalian cells are used as host cells, transfection generally is carried out by the calcium phosphate precipitation method, Graham, et al., Virology 52:546 (1978), Gorman, et al., DNA and Protein Eng. Tech. 2:3–10 (1990). However, other known methods for introducing DNA into prokaryotic and eukaryotic cells, such as nuclear injection, electroporation, or protoplast fusion also are suitable for use in this invention.

Particularly useful in this invention are expression vectors that provide for the transient expression in mammalian cells of DNA encoding human DNase II. In general, transient expression involves the use of an expression vector that is able to efficiently replicate in a host cell, such that the host cell accumulates many copies of the expression vector and, in turn, synthesizes high levels of a desired polypeptide encoded by the expression vector. Transient expression systems, comprising a suitable expression vector and a host cell, allow for the convenient positive identification of polypeptides encoded by cloned DNAs, as well as for the rapid screening of such polypeptides for desired biological or physiological properties. Wong, et al., Science 228:810–815 (1985); Lee, et al., Proc. Nat Acad. Sci. USA 82:4360–4364 (1985); Yang, et al., Cell 47:3–10 (1986). Thus, transient expression systems are conveniently used for expressing the DNA encoding amino acid sequence variants of human DNase II, in conjunction with assays to identify those variants that have such useful properties as increased half-life or decreased immunogenicity in vivo, or increased DNA hydrolytic activity at physiological pH.

Human DNase II preferably is secreted from the host cell in which it is expressed, in which case the variant is recovered from the culture medium in which the host cells are grown. In that case, it may be desirable to grow the cells in a serum free culture medium, since the absence of serum proteins and other serum components in the medium may facilitate purification of the variant. If it is not secreted, then the human DNase II is recovered from lysates of the host cells. When the human DNase II is expressed in a host cell other than one of human origin, the variant will be completely free of proteins of human origin. In any event, it will be necessary to purify the human DNase II from recombinant cell proteins in order to obtain substantially homogeneous preparations of the human DNase II. For therapeutic uses, the purified human DNase II preferably will be greater than 99% pure (i.e., any other proteins will comprise less than 1% of the total protein in the purified composition).

It is further contemplated that human DNase II may be produced by a method involving homologous recombination and amplification, for example, as described in PCT Patent Publication No. WO 91/06667, published May 16, 1991. Briefly, this method involves transforming cells containing an endogenous gene encoding human DNase II with a homologous DNA, which homologous DNA comprises (1) an amplifiable gene (e.g., a gene encoding dihydrofolate reductase (DHFR)), and (2) at least one flanking sequence, having a length of at least about 150 base pairs, which is homologous with a nucleotide sequence in the cell genome that is within or in proximity to the gene encoding human DNase II. The transformation is carried out under conditions such that the homologous DNA integrates into the cell genome by recombination. Cells having integrated the homologous DNA then are subjected to conditions which select for amplification of the amplifiable gene, whereby the human DNase II gene amplified concomitantly. The resulting cells then are screened for production of desired amounts of human DNase II. Flanking sequences that are in proximity to a gene encoding human DNase II are readily identified, for example, by the method of genomic walking, using as a starting point the nucleotide sequence of human DNase II shown in FIG. 1. Spoerel, et al., Meth. Enzymol. 152:598–603 (1987).

Generally, purification of human DNase II is accomplished by taking advantage of the differential physicochemical properties of the human DNase II as compared to the contaminants with which it may be associated. For example, as a first step, the culture medium or host cell lysate is centrifuged to remove particulate cell debris. The human DNase II thereafter is purified from contaminant soluble proteins and polypeptides, for example, by ammonium sulfate or ethanol precipitation, gel filtration (molecular exclusion chromatography), ion-exchange chromatography, hydrophobic chromatography, immunoaffinity chromatography (e.g., using a column comprising anti-human DNase II antibodies coupled to Sepharose), tentacle cation exchange chromatography (Frenz, et al., U.S. Pat. No. 5,279,823, issued Jan. 18, 1994), reverse phase HPLC, and/or gel electrophoresis.

In some host cells (especially bacterial host cells) the human DNase II may be expressed initially in an insoluble, aggregated form (referred to in the art as "refractile bodies" or "inclusion bodies") in which case it will be necessary to solubilize and renature the human DNase II in the course of its purification. Methods for solubilizing and renaturing recombinant protein refractile bodies are known in the art (see e.g., Builder, et al., U.S. Pat. No. 4,511,502, issued Apr. 16, 1985).

In another embodiment of this invention, covalent modifications are made directly to human DNase II to give it a desired property (for example, increased half-life or decreased immunogenicity in vivo, or increased DNA hydrolytic activity at physiological pH), and may be made instead of or in addition to the amino acid sequence substitution, insertion, and deletion mutations described above.

Covalent modifications are introduced by reacting targeted amino acid residues of human DNase II with an organic derivatizing agent that is capable of reacting with selected amino acid side-chains or N- or C-terminal residues. Suitable derivatizing agents and methods are well known in the art. Covalent coupling of glycosides to amino acid residues of the protein may be used to modify or increase the number or profile of carbohydrate substituents.

The covalent attachment of agents such as polyethylene glycol (PEG) or human serum albumin to human DNase II may reduce immunogenicity and/or toxicity of the human DNase II and/or prolong its half-life, as has been observed with other proteins. Abuchowski, et al., J. Biol. Chem. 252:3582–3586 (1977); Poznansky, et al., FEBS Letters 239:18–22 (1988); Goodson, et al., Biotechnology 8:343–346 (1990); Katre, J. Immunol. 144:209–213 (1990); Harris, *Polyethylene Glycol Chemistry* (Plenum Press, 1992). As another example, the variant or modified form of human DNase II may comprise an amino acid sequence mutation or other covalent modification that reduces the susceptibility of the variant to degradation by proteases (e.g., neutrophil elastase) that may be present in sputum and other biological materials, as compared to human DNase II.

Antibodies to human DNase II are produced by immunizing an animal with human DNase II or a fragment thereof, optionally in conjunction with an immunogenic polypeptide, and thereafter recovering antibodies from the serum of the immunized animals. Alternatively, monoclonal antibodies are prepared from cells of the immunized animal in conventional fashion. The antibodies also can be made in the form of chimeric (e.g., humanized) or single chain antibodies or Fab fragments, using methods well known in the art. Preferably, the antibodies will bind to human DNase II but will not substantially bind to (i.e., cross react with) other DNase proteins (such as human and bovine DNase I). The antibodies can be used in methods relating to the localization and activity of human DNase II, for example, for detecting human DNase II and measuring its levels in tissues or clinical samples. Immobilized anti-human DNase II antibodies are particularly useful in the detection of human DNase II in clinical samples for diagnostic purposes, and in the purification of human DNase II.

Purified human DNase II is used to reduce the viscoelasticity of DNA-containing material, such as sputum, mucus, or other pulmonary secretions. human DNase II is particularly useful for the treatment of patients with pulmonary disease who have abnormal viscous or inspissated secretions and conditions such as acute or chronic bronchial pulmonary disease, including infectious pneumonia, bronchitis or tracheobronchitis, bronchiectasis, cystic fibrosis, asthma, tuberculosis, and fungal infections. For such therapies, a solution or finely divided dry preparation of the human DNase II is instilled in conventional fashion into the airways (e.g., bronchi) or lungs of a patient, for example by aerosolization.

Human DNase II also is useful for adjunctive treatment of abscesses or severe closed-space infections in conditions such as empyema, meningitis, abscess, peritonitis, sinusitis, otitis, periodontitis, pericarditis, pancreatitis, cholelithiasis, endocarditis and septic arthritis, as well as in topical treatments in a variety of inflammatory and infected lesions such as infected lesions of the skin and/or mucosal membranes, surgical wounds, ulcerative lesions and burns. Human DNase II may improve the efficacy of antibiotics used in the treatment of such infections (e.g., gentamicin activity is markedly reduced by reversible binding to intact DNA).

Human DNase II also is useful for preventing the new development and/or exacerbation of respiratory infections, such as may occur in patients having cystic fibrosis, chronic bronchitis, asthma, pneumonia, or other pulmonary disease, or patients whose breathing is assisted by ventilator or other mechanical device, or other patients at risk of developing respiratory infections, for example post-surgical patients.

Human DNase II also is useful for the treatment for systemic lupus erythematosus (SLE), a life-threatening autoimmune disease characterized by the production of diverse autoantibodies. DNA is a major antigenic component of the immune complexes. In this instance, the human DNase II may be given systemically, for example by intravenous, subcutaneous, intrathecal, or intramuscular administration to the affected patient.

Finally, human DNase II is useful for the treatment of other non-infected conditions in which there is an accumulation of cellular debris that includes cellular DNA, such as pyelonephritis and tubulo-interstitial kidney disease.

Human DNase II can be formulated according to known methods to prepare therapeutically useful compositions. Typically, the human DNase II is formulated with a physiologically acceptable excipient (or carrier) for therapeutic use. Such excipients are used, for example, to provide liquid formulations and sustained-release formulations of human DNase II. The human DNase II formulation may be used with commercially-available nebulizers including jet nebulizers and ultrasonic nebulizers for administration of the DNase II directly into the airways or lungs of an affected patient. Another preferred therapeutic composition is a dry powder of human DNase II, preferably prepared by spray-drying of a solution of the human DNase II, essentially as described in co-pending U.S. patent application Ser. No. 08/206,020 (filed Mar. 4, 1994). In all cases, it is desirable that the therapeutic compositions of DNase II be sterile. Preferably, the therapeutic compositions are disposed in a container fabricated of plastic or other non-glass material.

In a further embodiment, the therapeutic composition comprises cells actively producing human DNase II. Such cells may be directly introduced into the tissue of a patient, or may be encapsulated within porous membranes which are then implanted in a patient (see e.g., Aebischer, et al., U.S. Pat. No. 4,892,538, issued Jan. 9, 1990; Aebischer, et al., U.S. Pat. No. 5,283,187, issued Feb. 1, 1994), in either case providing for the delivery of the human DNase II into areas within the body of the patient in need of increased concentrations of DNA-hydrolytic activity. In one embodiment of the invention, the patient's cells are transformed, either in vivo or ex vivo, with DNA encoding human DNase II, and then used to produce the human DNase II directly within the patient. This latter method is commonly referred to as gene therapy. In another embodiment, the patient's cells are transformed with other DNA (such as a promoter, enhancer, or amplifiable gene) that is capable of activating or increasing expression of an endogenous human DNase II gene.

In certain circumstances, it may be desirable to decrease the amount of human DNase II expressed in a cell. For that purpose, human DNase II anti-sense oligonucleotides can be made and a method utilized for diminishing the level of human DNase II within the cell comprising introducing into the cell one or more human DNase II anti-sense oligonucleotides. The term "human DNase II anti-sense oligonucleotide" refers to an oligonucleotide that has a nucleotide sequence that is capable of interacting through base pairing with a complementary nucleotide sequence that is involved in the expression of human DNase II within a cell, and thereby interfering with such expression.

The therapeutically effective amount of human DNase II will depend, for example, upon the amount of DNA in the material to be treated, the therapeutic objectives, the route of administration, and the condition of the patient. Accordingly, it will be necessary for the therapist to titer the dosage and modify the route of administration as required to obtain the optimal therapeutic effect. Generally, the therapeutically effective amount of human DNase II will be a dosage of from about 0.1 $\mu$g to about 5 mg of the variant per kilogram of body weight of the patient, administered within pharmaceutical compositions, as described herein.

Human DNase II optionally is combined with or administered in concert with one or more other pharmacologic agents used to treat the conditions listed above, such as antibiotics, bronchodilators, anti-inflammatory agents, mucolytics (e.g. n-acetyl-cysteine), actin binding or actin severing proteins (e.g., gelsolin; Matsudaira et al., Cell 54:139–140 (1988); Stossel, et al., PCT Patent Publication No. WO 94/22465, published Oct. 13, 1994; protease inhibitors; or gene therapy product (e.g., comprising the cystic fibrosis transmembrane conductance regulator (CFTR) gene); Riordan, et al., Science 245:1066–1073 (1989)).

This invention also provides methods for determining the presence of a nucleic acid molecule encoding human DNase II in test samples prepared from cells, tissues, or biological fluids, comprising contacting the test sample with isolated DNA comprising all or a portion of the nucleotide coding sequence for human DNase II and determining whether the isolated DNA hybridizes to a nucleic acid molecule in the test sample. DNA comprising all or a portion of the nucleotide coding sequence for human DNase II is also used in hybridization assays to identify and to isolate nucleic acids sharing substantial sequence identity to the coding sequence for human DNase II, such as nucleic acids that encode naturally-occurring allelic variants of human DNase II.

Also provided is a method for amplifying a nucleic acid molecule encoding human DNase II that is present in a test sample, comprising the use of an oligonucleotide having a portion of the nucleotide coding sequence for human DNase II as a primer in a polymerase chain reaction.

The following examples are offered by way of illustration only and are not intended to limit the invention in any manner. All patent and literature references cited herein are expressly incorporated.

EXAMPLE 1

Cloning Human DNase II cDNA

Full-length cDNA encoding human DNase II was identified by screening a human placental cDNA library (in λ-gt11, Clontech, Palo Alto, Calif. USA) with a mixture of the following oligonucleotide probes, each of which had been end-labeled with T4 polynucleotide kinase and $\gamma$-$^{32}$P-adenosine triphosphate to a high specific radioactivity:

5'-GCCCAGAGAGGGCTGCAGTACAAGTATCTGGA-CGAGAGCTCCGGAGGC-3' (SEQ. ID. NO: 3)

5'-CCCAGCGCCCGCAGTCCCAGACACAGATTCC-TGGATCTCAGCCC-3 (SEQ. ID. NO: 4)

5'-GAYCARGARGGNGGNTTYTGGCTNAT-3' (SEQ. ID. NO: 5)

5'-GAYCARGARGGNGGNTTYTGGTTRAT-3' (SEQ. ID. NO: 6)

5'-AAYCGNGGNCAYACNAARGGNGT-3' (SEQ. ID. NO: 7)

5'-AAYAGRGGNCAYACNAARGGNGT-3' (SEQ. ID. NO: 8)

The first two of the oligonucleotide probes listed above (SEQ. ID. NOS: 3 and 4) comprise portions of the EST sequence having accession code T53394, in the Genbank database.

Hybridization of the probes to the cDNA library was carried out under low stringency conditions (in 20% vol/vol formamide, 5×SSPE, 5×Denhardt's solution, 0.1% sodium dodecyl sulfate (SDS), and 100 µg/ml sonicated salmon sperm DNA), at 42° C., for 20 hours. Post hybridization washes were carried out in 2×SSC, 0.1% SDS, at 42° C. 1×SSPE is 150 mM NaCl, 10 mM sodium phosphate, 1 mM EDTA, pH 7.4. 1×Denhardt's solution is 0.02% Ficoll, 0.02% bovine serum albumin, and 0.02% polyvinyl-pyrrolidone. 1×SSC is 0.15 M NaCl, 0.015 M sodium citrate, pH 7.0.

Hybridization-positive phage clones were isolated and their DNAs sequenced following standard procedures. A 1575 base-pair insert was identified amongst the hybridization-positive phage clones, including an open reading frame of 1080 base-pairs that encodes a predicted protein that is 360 amino acid residues in length. The nucleotide sequence of the 1575 base-pair insert (SEQ. ID. NO: 1) and the amino acid sequence of predicted protein (SEQ. ID. NO: 2) are shown in FIG. 1.

The predicted protein includes a signal sequence that is 16 amino acid residues in length. Cleavage of the signal sequence releases the mature protein (human DNase II) that is 344 amino acid residues in length, and that has a predicted molecular weight of 38,000 Daltons and a predicted pI of 9.0.

EXAMPLE 2

Expression of Human DNase II cDNA

The cDNA encoding human DNase II was subcloned into a mammalian expression vector pRK5 (Gorman, et al., DNA and Protein Engineering Techniques 2:1 (1990); European Patent Publication EP 307,247, published Mar. 15, 1989). The resulting recombinant vector is referred to as pRK5/human DNase II. Human embryonic kidney 293 cells (American Type Culture Collection, CRL 1573) were grown in serum-containing Dulbecco Modified Eagle's medium (DMEM) to 70% confluency and then transiently transfected with pRK5/human DNase II, or as a control, pRK5 alone. 24 hours post-transfection, the cells were washed with phosphate buffered saline and transferred to serum-free medium containing insulin. 72–96 hours later, conditioned medium was collected from the cell cultures and concentrated approximately 10-fold. Proteins expressed in the cell cultures were analyzed by SDS-polyacrylamide gel electrophoresis (SDS-PAGE).

Cells transfected with pRK-5/human DNase II were found to produce a unique protein of about 42,000–44,000 Daltons, that was not produced in cells transfected with pRK5 alone.

The amino-terminal sequence of that secreted protein was determined by preparing a poly-His tagged version of human DNase II. DNA encoding the poly-His tagged version of human DNase II was prepared by joining a nucleotide sequence encoding the amino acid sequence.

Met-Arg-Gly-Ser-His-His-His-His-His-His (SEQ. ID. NO: 9) to the 3' end of the nucleotide sequence encoding human DNase II that is shown in FIG. 1. Human embryonic kidney 293 cells were transiently transfected with the DNA, and Ni-NTA-silica (Qiagen, Inc., Chatsworth, Calif. USA) was used to purify the secreted poly-His tagged human DNase II. The amino-terminal amino acid sequence of the secreted protein was determined to be Leu-Thr-Cys-Tyr-Gly-Asp-Ser-Gly-Gln (SEQ. ID. NO: 10), in agreement with the predicted amino acid sequence of the mature human DNase II protein shown in FIG. 1. used to purify the secreted poly-His tagged human DNase II. The amino-terminal amino acid sequence of the secreted protein was determined to be Leu-Thr-Cys-Tyr-Gly-Asp-Ser-Gly-Gln, in agreement with the predicted amino acid sequence of the mature human DNase II protein shown in FIG. 1.

EXAMPLE 3

Biological Activity of Human DNase II

Concentrated cell culture supernatants, prepared as described above, were tested for DNA-hydrolytic activity in a hyperchromicity assay (Kunitz, J. Gen. Physiol. 33:349–362 (1950); Kunitz, J. Gen. Physiol. 33:363–377 (1950)), in which the buffer used was 0.1M sodium acetate, pH 4.6, 1 mM magnesium chloride. Such activity was detected in the supernatants from cells transfected with pRK5/human DNase II, but not in the supernatants from cells transfected with pRK5 alone. By also assaying cell lysates, it was determined that approximately 20%–30% of the total human DNase II activity in the cells transfected with pRK5/human DNase was secreted.

EXAMPLE 4

Pattern of Expression of Human DNase II in Human Tissue

Northern blots of various human tissues were performed using a radiolabeled probe comprising a portion of the coding sequence of the cloned human DNase II cDNA. Expression of human DNase II messenger RNA (mRNA) was found in all tissues examined (brain, colon, heart, small intestine, kidney, liver, lung, peripheral blood lymphocytes, skeletal muscle, ovary, pancreas, placenta, prostate, spleen, testis, and thymus).

What is claimed is:

1. An isolated polypeptide comprising the amino acid residues 1 to 344 of (SEQ ID NO: 2).

2. A method for the treatment of a patient having a pulmonary disease or disorder comprising administering to the patient a therapeutically effective amount of a polypeptide according to claim 1.

3. The method of claim 2 wherein the disease or disorder is cystic fibrosis.

4. A method for the treatment of a patient having systemic lupus erythematosus comprising administering to the patient a therapeutically effective amount of a polypeptide according to claim 1.

* * * * *

```
                              SEQUENCE LISTING (1) GENERAL INFORMATION:

(iii) NUMBER OF SEQUENCES: 10

(2) INFORMATION FOR SEQ ID NO: 1:

(i) SEQUENCE CHARACTERISTICS:
        (A) LENGTH: 1575 base pairs
        (B) TYPE: Nucleic Acid
        (C) STRANDEDNESS: Single
        (D) TOPOLOGY: Linear (ii) MOLECULE TYPE: DNA (xi) SEQUENCE DESCRIPTION: SEQ ID NO: 1:

GAATTCGGGC CAGTCCTGGC CTCTGATGTA ACCCAGCGCC CCGCAGTCCC              50

GACACAGATT CCTGGATCTC AGCCCCATAG CAGCTATGAT CCCGCTGCTG             100

CTGGCAGCGC TGCTGTGCGT CCCCGCCGGG GCCCTGACCT GCTACGGGGA             150

CTCCGGGCAG CCTGTAGACT GGTTCGTGGT CTACAAGCTG CCAGCTCTTA             200

GAGGGTCCGG GGAGGCGGCG CAGAGAGGGC TGCAGTACAA GTATCTGGAC             250

GAGAGCTCCG GAGGCTGGCG GGACGGCAGG GCACTCATCA ACAGCCCGGA             300

GGGGGCCGTG GGCCGAAGCC TGCAGCCGCT GTACCGGAGC AACACCAGCC             350

AGCTCGCCTT CCTGCTCTAC AATGACCAAC CGCCTCAACC CAGCAAGGCT             400

CAGGACTCTT CCATGCGTGG GCACACGAAG GGTGTCCTGC TCCTTGACCA             450

CGATGGGGGC TTCTGGCTGG TCCACAGTGT ACCTAACTTC CCTCCACCGG             500

CCTCCTCTGC TGCATACAGC TGGCCTCATA GCGCCTGTAC CTACGGGCAG             550

ACCCTGCTCT GTGTGTCTTT TCCCTTCGCT CAGTTCTCGA AGATGGGCAA             600

GCAGCTGACC TACACCTACC CCTGGGTCTA TAACTACCAG CTGGAAGGGA             650

TCTTTGCCCA GGAATTCCCC GACTTGGAGA ATGTGGTCAA GGGCCACCAC             700

GTTAGCCAAG AACCCTGGAA CAGCAGCATC ACACTCACAT CCCAGGCCGG             750

GGCTGTTTTC CAGAGCTTTG CCAAGTTCAG CAAATTTGGA GATGACCTGT             800

ACTCCGGCTG GTTGGCAGCA GCCCTTGGTA CCAACCTGCA GGTCCAGTTC             850

TGGCACAAAA CTGTAGGCAT CCTGCCCTCT AACTGCTCGG ATATCTGGCA             900

GGTTCTGAAT GTGAACCAGA TAGCTTTCCC TGGACCAGCC GGCCCAAGCT             950

TCAACAGCAC AGAGGACCAC TCCAAATGGT GCGTGTCCCC AAAAGGGCCC            1000

TGGACCTGCG TGGGTGACAT GAATCGGAAC CAGGGAGAGG AGCAACGGGG            1050

TGGGGGCACA CTGTGTGCCC AGCTGCCAGC CCTCTGGAAA GCCTTCCAGC            1100

CGCTGGTGAA GAACTACCAG CCCTGTAATG GCATGGCCAG GAAGCCCAGC            1150

AGAGCTTATA AGATCTAACC CTTATGGCCA GGTGCAGTGG CTCACGTATG            1200

TAATCCCAGC ACTTTGGGAA GCCAAGGAGG GAGGATCACT TGAACTCAGG            1250

AATTCGAGAC CAGCCTGGGC TACATAGTGA GACCACATCT CTACTAGAAC            1300

TTAAAAAAAG TTAGCCAGGC ACGGTGATAA ATGCCTGTAG TCCCAGCCAC            1350
```

```
                                                    -continued

TGAAGCCAGA GGATCGATTG AACCAGGGAG ATCATGGTCA CAGTGAACTA              1400

TGATTACGCC AACCTGGGTC ACATAGCAAG ACTCTGTTTC AAAAAAAAAG              1450

GGGGGGCGGG GGACGGGTGG GTGCAGTGGC TCACATCTGT AACCCCAGCA              1500

CTTTGGGAGG CTGAGATGGG CAGATCACTT GAGGTCAGGA GTTCGAGACC              1550

AGCCTGGCCA ACATGGTGAA ACCCC                                        1575
```

(2) INFORMATION FOR SEQ ID NO: 2:

(i) SEQUENCE CHARACTERISTICS:
        (A) LENGTH: 360 amino acids
        (B) TYPE: Amino Acid
        (D) TOPOLOGY: Linear (xi) SEQUENCE DESCRIPTION: SEQ ID NO: 2:

```
Met Ile Pro Leu Leu Ala Ala Leu Leu Cys Val Pro Ala Gly
 1               5                  10                  15

Ala Leu Thr Cys Tyr Gly Asp Ser Gly Gln Pro Val Asp Trp Phe
            20                  25                  30

Val Val Tyr Lys Leu Pro Ala Leu Arg Gly Ser Gly Glu Ala Ala
            35                  40                  45

Gln Arg Gly Leu Gln Tyr Lys Tyr Leu Asp Glu Ser Ser Gly Gly
            50                  55                  60

Trp Arg Asp Gly Arg Ala Leu Ile Asn Ser Pro Glu Gly Ala Val
            65                  70                  75

Gly Arg Ser Leu Gln Pro Leu Tyr Arg Ser Asn Thr Ser Gln Leu
            80                  85                  90

Ala Phe Leu Leu Tyr Asn Asp Gln Pro Gln Pro Ser Lys Ala
            95                 100                 105

Gln Asp Ser Ser Met Arg Gly His Thr Lys Gly Val Leu Leu Leu
           110                 115                 120

Asp His Asp Gly Gly Phe Trp Leu Val His Ser Val Pro Asn Phe
           125                 130                 135

Pro Pro Pro Ala Ser Ser Ala Ala Tyr Ser Trp Pro His Ser Ala
           140                 145                 150

Cys Thr Tyr Gly Gln Thr Leu Leu Cys Val Ser Phe Pro Phe Ala
           155                 160                 165

Gln Phe Ser Lys Met Gly Lys Gln Leu Thr Tyr Thr Tyr Pro Trp
           170                 175                 180

Val Tyr Asn Tyr Gln Leu Glu Gly Ile Phe Ala Gln Glu Phe Pro
           185                 190                 195

Asp Leu Glu Asn Val Val Lys Gly His His Val Ser Gln Glu Pro
           200                 205                 210

Trp Asn Ser Ser Ile Thr Leu Thr Ser Gln Ala Gly Ala Val Phe
           215                 220                 225

Gln Ser Phe Ala Lys Phe Ser Lys Phe Gly Asp Asp Leu Tyr Ser
           230                 235                 240

Gly Trp Leu Ala Ala Ala Leu Gly Thr Asn Leu Gln Val Gln Phe
           245                 250                 255

Trp His Lys Thr Val Gly Ile Leu Pro Ser Asn Cys Ser Asp Ile
           260                 265                 270

Trp Gln Val Leu Asn Val Asn Gln Ile Ala Phe Pro Gly Pro Ala
           275                 280                 285

Gly Pro Ser Phe Asn Ser Thr Glu Asp His Ser Lys Trp Cys Val
           290                 295                 300
```

```
Ser Pro Lys Gly Pro Trp Thr Cys Val Gly Asp Met Asn Arg Asn
            305                 310                 315

Gln Gly Glu Glu Gln Arg Gly Gly Gly Thr Leu Cys Ala Gln Leu
            320                 325                 330

Pro Ala Leu Trp Lys Ala Phe Gln Pro Leu Val Lys Asn Tyr Gln
            335                 340                 345

Pro Cys Asn Gly Met Ala Arg Lys Pro Ser Arg Ala Tyr Lys Ile
            350                 355                 360

(2) INFORMATION FOR SEQ ID NO: 3:

(i) SEQUENCE CHARACTERISTICS:
        (A) LENGTH: 48 base pairs
        (B) TYPE: Nucleic Acid
        (C) STRANDEDNESS: Single
        (D) TOPOLOGY: Linear (xi) SEQUENCE DESCRIPTION: SEQ ID NO: 3:

GCCCAGAGAG GGCTGCAGTA CAAGTATCTG GACGAGAGCT CCGGAGGC                48

(2) INFORMATION FOR SEQ ID NO: 4:

(i) SEQUENCE CHARACTERISTICS:
        (A) LENGTH: 45 base pairs
        (B) TYPE: Nucleic Acid
        (C) STRANDEDNESS: Single
        (D) TOPOLOGY: Linear (xi) SEQUENCE DESCRIPTION: SEQ ID NO: 4:

CCCAGCGCCC CGCAGTCCCA GACACAGATT CCTGGATCTC AGCCC                   45

(2) INFORMATION FOR SEQ ID NO: 5:

(i) SEQUENCE CHARACTERISTICS:
        (A) LENGTH: 26 base pairs
        (B) TYPE: Nucleic Acid
        (C) STRANDEDNESS: Single
        (D) TOPOLOGY: Linear (xi) SEQUENCE DESCRIPTION: SEQ ID NO: 5:

GAYCARGARG GNGGNTTYTG GCTNAT                                        26

(2) INFORMATION FOR SEQ ID NO: 6:

(i) SEQUENCE CHARACTERISTICS:
        (A) LENGTH: 26 base pairs
        (B) TYPE: Nucleic Acid
        (C) STRANDEDNESS: Single
        (D) TOPOLOGY: Linear (xi) SEQUENCE DESCRIPTION: SEQ ID NO: 6:

GAYCARGARG GNGGNTTYTG GTTRAT                                        26

(2) INFORMATION FOR SEQ ID NO: 7:

(i) SEQUENCE CHARACTERISTICS:
        (A) LENGTH: 23 base pairs
        (B) TYPE: Nucleic Acid
        (C) STRANDEDNESS: Single
        (D) TOPOLOGY: Linear (xi) SEQUENCE DESCRIPTION: SEQ ID NO: 7:

AAYCGNGGNC AYACNAARGG NGT                                           23
```

-continued (2) INFORMATION FOR SEQ ID NO: 8:

(i) SEQUENCE CHARACTERISTICS:
        (A) LENGTH: 23 base pairs
        (B) TYPE: Nucleic Acid
        (C) STRANDEDNESS: Single
        (D) TOPOLOGY: Linear (xi) SEQUENCE DESCRIPTION: SEQ ID NO: 8:

AAYAGRGGNC AYACNAARGG NGT        23

(2) INFORMATION FOR SEQ ID NO: 9:

(i) SEQUENCE CHARACTERISTICS:
        (A) LENGTH: 10 amino acids
        (B) TYPE: Amino Acid
        (D) TOPOLOGY: Linear (xi) SEQUENCE DESCRIPTION: SEQ ID NO: 9:

Met Arg Gly Ser His His His His His His
1               5                   10

(2) INFORMATION FOR SEQ ID NO: 10:

(i) SEQUENCE CHARACTERISTICS:
        (A) LENGTH: 9 amino acids
        (B) TYPE: Amino Acid
        (D) TOPOLOGY: Linear (xi) SEQUENCE DESCRIPTION: SEQ ID NO: 10:

Leu Thr Cys Tyr Gly Asp Ser Gly Gln
1               5